United States Patent [19]

Dowd et al.

[11] 4,237,304

[45] Dec. 2, 1980

[54] OXAZOLINIUM SALTS AND METHOD OF PREPARATION

[75] Inventors: William Dowd; Richard C. Krauss; Edward R. Freiter, all of Midland, Mich.

[73] Assignee: The Dow Chemical Company, Midland, Mich.

[21] Appl. No.: 955,039

[22] Filed: Oct. 26, 1978

Related U.S. Application Data

[62] Division of Ser. No. 611,109, Sep. 8, 1975.

[51] Int. Cl.$^3$ .................. C07D 263/12; C07D 263/14
[52] U.S. Cl. .................................. 548/239; 260/570.6
[58] Field of Search ...................... 260/307 F; 548/239

[56] References Cited

U.S. PATENT DOCUMENTS

| | | | |
|---|---|---|---|
| 2,513,346 | 7/1950 | Moersch et al. | 260/307 F |
| 2,530,627 | 11/1950 | Pfister et al. | 260/307 F |
| 2,564,423 | 8/1951 | Barnum | 260/307 F |
| 2,714,082 | 7/1955 | Davies et al. | 260/307 F |
| 3,278,544 | 10/1966 | Easton | 260/307 F |
| 4,024,184 | 5/1977 | Kaiser et al. | 260/307 F |

*Primary Examiner*—Anton H. Sutto

[57] ABSTRACT

1-Aryl-1-hydroxy-2-methylaminopropanes are rearranged from the erythro isomer to the threo isomer by the process of (1) forming the O,N-diacyl derivative of the arylpropanolamine; (2) reacting the product of step (1) with an anhydrous or substantially anhydrous protic acid (thereby forming a novel oxazolinium salt); and (3) reacting the oxazolinium salt from step (2) with an aqueous protic acid. The threo isomer of the arylpropanolamine is thus produced as an amine/acid salt. This salt can be further purified, if desired, by neutralizing the acid/amine salt with caustic isolating the free amine and reprotonating the free base in isopropanol with, for example, anhydrous HCl. This process is particularly applicable to manufacture of d-pseudoephedrine from 1-ephedrine.

7 Claims, No Drawings

OXAZOLINIUM SALTS AND METHOD OF PREPARATION

This is a division of application Ser. No. 611,109, filed Sept. 8, 1975.

BACKGROUND OF THE INVENTION

The 1-aryl-1-hydroxy-2-methylaminopropanes are optically active compounds which are pharmaceutically useful. Unfortunately, one stereo isomer is generally the active component while the other isomer is either inert, less effective or deactivating.

One of the most important 1-aryl-1-hydroxy-2-methylaminopropane is d-pseudoephedrine. It has been heretofore prepared by several methods from 1-ephedrine. For example, treatment of 1-ephedrine with aqueous HCl gave a diasteriomeric mixture of approximately 40 percent 1-ephedrine and 60 percent d-pseudoephedrine after rather long reaction times (e.g. 40 hours) and elevated temperatures. Separation of such optical isomers is tedious, time consuming, and has heretofore proceeded in rather low yields. Emde, Helv. Chem. Acta., 12, 377 (1929).

In yet another process, 1-ephedrine was converted to its monoacetate (amide) and hydrolyzed to give again a diasteriomeric mixture of approximately 35 percent 1-ephedrine and approximately 65 percent d-pseudoephedrine. Welsh, J. Am. Chem. Soc., 69, 128 (1947).

It has also been reported that the reaction of 1-ephedrine hydrochloride with 10 moles excess acetic anhydride gave d-pseudoephedrine hydrochloride. No yields were reported. Schmidt and Calliess, Arch. Pharm., 250, 154 (1912).

It was also reported that the reaction of 1-ephedrine with o-methylbenzoyl chloride and subsequent hydrolysis of the resulting amide gave d-pseudoephedrine. Welsh, J. Am. Chem. Soc., 71, 3500 (1949).

SUMMARY OF THE INVENTION

We have discovered a novel process for converting erythro isomers of 1-aryl-1-hydroxy-2-methylaminopropanes selectively to the corresponding threo isomer. Our process comprises the steps of:
(1) reacting by contacting the erythro isomer or a diasteriomeric mixture (racemic or optically pure) of a 1-aryl-1-hydroxy-2-methylaminopropane with at least two equivalents of an organic acylating reagent; thereby forming the O,N-diacylated derivative;
(2) reacting by contacting said O,N-diacylated derivative with an anhydrous or substantially anhydrous protic acid; thereby forming an oxazolinium salt; and
(3) reacting said oxazolinium salt with an aqueous protic acid to form the corresponding threo isomer as an acid/amine salt.

The product of step (3) can be further purified, if desired, by reacting it with a base (such as sodium hydroxide) to form the free amine, thereafter recovering the free amine by crystallization from an organic solvent or water where the threo isomer selectively precipitates from solution as an essentially pure free amine, dissolving said free amine in isopropanol, and reacting the amine/isopropanol solution with a protic acid—thus precipitating the threo isomer as the essentially pure acid/amine salt.

The above process produces the desired threo isomers of 1-aryl-1-hydroxy-2-methylaminopropanes in extremely high yields and purity. The process is particularly useful in forming d-pseudoephedrine from 1-ephedrine.

DETAILED DESCRIPTION OF THE INVENTION

Step I

In Step I, the O,N-diacyl derivative of 1-aryl-1-hydroxy-2-methylaminopropane is formed. This step is conducted by reacting by contacting the erythro isomer of said arylpropanolamine with at least about 2 equivalents of an acylating reagent per mole of said arylpropanolamine. The reactants used in this step are well known classes of reactants having many members, any member of which can be used herein.

The arylpropanolamine reactant, for example, may be the optically pure erythro isomer or it may be a racemic mixture of the erythro isomer. Also, the erythro isomer may be used singly or in combination as a diasteriomeric mixture with the threo isomer in the instant process. This is commercially significant for in many instances the arylpropanolamines may be formed as diasteriomeric mixtures which can be used without separation of the isomers. From this, we conclude that the instant process is essentially nonreversible and stereo specific. Illustrative examples of this class of compounds include 1-phenyl-1-hydroxy-2-methylaminopropane and 1-(inertly-substituted) phenyl-1-hydroxy-2-methylaminopropanes, such as 1-chlorophenyl-1-methoxyphenyl-, 1-methylphenyl-, 1-butylphenyl-1-hydroxy-2-methylaminopropane, and the like.

The acylating reagent used in the process may be varied to convenience so long as the O,N-diacyl derivative of the arylpropanolamine is formed. Conventional acylating reagents include: ketenes; carboxylic acids (e.g. acetic acid, propionic acid, butenoic acid, octanoic acid, etc.); acyl chlorides (e.g. acetyl chloride, propanoyl chloride, benzoyl chloride, etc.); acid anhydrides (e.g. acetic anhydride, propionic anhydride, benzoic anhydride, phthalic anhydride, etc.); carboxylic acid esters (e.g. methyl and ethyl esters of acetic acid, propionic acid, butyric acid, hexanoic acid, etc.); and the like. The preferred acylating reagents are acid anhydrides of organic monocarboxylic acids having from 2 to about 8 carbon atoms. Of these, acetic anhydride and propionic anhydride are preferred with acetic anhydride representing the most preferred acylating reagent.

The stoichiometry of this reaction requires two equivalents of the acylating reagent per mole of arylpropanolamine reactant. Normally, we prefer to use a slight excess of acylating reagent to insure maximum conversion of the arylpropanolamine to the corresponding O,N-diacylated derivative thereof. Thus, we normally use from about 2 to about 5 equivalents of acylating reagent per mole of arylpropanolamine.

The reaction may be conducted neat but it is preferably conducted in the presence of an inert liquid, water immiscible organic solvent or diluent. By "inert" is meant that the reaction solvent or diluent is inert in the process. Suitable such solvents and diluents include hydrocarbons (e.g. benzene, toluene, octane, petroleum ether, etc.), inertly-substituted hydrocarbons (e.g. chlorobenzene, dichlorobenzene, perchloroethylene, methoxytoluene, etc.), and the like. Toluene is the solvent of choice. When a solvent or reaction diluent is used, the product yield is substantially improved by conducting the reaction under essentially anhydrous conditions.

The reaction rate will, of course, vary with temperature, degree of reactivity of the particular combination of reactants, etc. However, we have observed that normally an acceptable rate of reaction is obtained at temperatures of from about 100° to about 120° C. and that the refluxing temperature of the reaction mixture in toluene is normally quite satisfactory. Under these conditions, the reaction is generally complete in from about 4 to about 10 hours.

Step II

In this step, the O,N-diacyl derivative of the arylpropanolamine from Step I is contacted with an anhydrous or essentially anhydrous protic acid. Essentially any protic acid can be used which is of sufficient acid strength to protonate the amine but we normally prefer to use a strong inorganic protic acid (e.g. HCl, HBr, $H_2SO_4$, $HClO_4$, etc). HCl is presently the current acid of choice. This step likewise can be conducted neat but is preferably conducted in the presence of an inert reaction solvent or diluent with toluene again being the solvent of choice. The stoichiometry of the reaction occurring here requires one equivalent of acid per mol of O,N-diacyl derivative of the arylpropanolamine. This reaction is likewise best conducted under anhydrous or substantially anhydrous conditions.

The product of this step is a novel oxazolinium salt. This oxazolinium salt can be represented by the formula

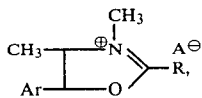

wherein R is the organic residue of the acylating reagent, Ar is a monovalent aromatic radical and $A^\ominus$ is an inert neutralizing anion. For example, R is methyl when acetic anhydride is used, R is ethyl when propionic anhydride is used, etc. These oxazolinium salts are new compounds which are useful as reaction intermediates in the formation of the threo isomers of 1-aryl-1-hydroxy-2-methylaminopropanes. Such oxazolinium salts can be isolated by crystallization from the reaction medium but are normally prepared and used in solution. The anion, $A^\ominus$, can be varied by the choice of acid used in Step II to protonate the amine, or, the anion can be varied by conventional ion-exchange techniques. $A^\ominus$ is preferably $Cl^\ominus$ since HCl is the acid of choice in Step II.

Step III

In this step, the oxazolinium salt from Step II is hydrolyzed with an aqueous protic acid to give the desired threo 1-aryl-1-hydroxy-2-methylaminopropane as an acid/amine salt. This step is conducted by merely adding an aqueous protic acid (e.g. aqueous HCl) to the oxazolinium salt or to the reaction medium containing the oxazolinium salt. The reaction rate of the hydrolysis will vary depending upon the particular oxazolinium salt and acid concentration. For example, the reaction is normally complete in from about 4 to about 6 hours at temperatures in the range of from about 80° to about 100° C. using 0.25 equivalents of acid per mole of oxazolinium salt. The product as the acid/amine salt can be precipitated by concentrating the reaction mixture under reduced pressure and subsequently cooling the reaction mixture until the solid amine/acid salt precipitates. The acid/amine salt thus obtained is relatively pure.

Alternatively, however, the reaction mixture from Step III, containing the aqueous solution of the acid/amine salt and the inert solvent (e.g. toluene) as a heterogenous mixture, is blended with sufficient strong base (e.g. sodium hydroxide, potassium hydroxide, etc.) to form the 1-aryl-1-hydroxy-2-methylaminopropane as a free amine. This mixture is normally heated, allowing the free amine to completely pass into solution in the inert solvent. The mixture is then phase separated and the organic phase containing the amine cooled. The pure threo isomer of the free amine crystallizes from the cooled solution. Preferably, the organic phase containing the amine is dried before or during cooling (e.g. by azeotropic distillation).

The following experimental information will further illustrate the invention. All "parts" are parts by weight unless otherwise specified in the examples.

EXPERIMENT 1

Preparation of d-pseudoephedrine from l-ephedrine

Preparation of starting material: l-ephedrine hydrochloride (110 parts) was added to toluene (236 parts) and 50 percent aqueous sodium hydroxide (45 parts). The solution was heated to approximately 40° C. and the aqueous and organic phases thus formed were separated. The lower aqueous brine layer was discarded and the upper toluene layer containing l-ephedrine was dried by azeotropic distillation. Step I: The dried toluene solution was then blended with acetic anhydride (117 parts) and the resulting reaction mixture heated at 113°–118° C. for 6 to 7 hours. Step II: Then, anhydrous hydrochloric acid (20 parts) was added to the stirred solution over a 1.5 hour period and the reaction mixture heated at 90° C. for an additional hour. Step III: Next, 165 parts of aqueous HCl (160 parts of water and 5 parts of HCl) was added to the reaction mixture and the stirred mixture again heated at 90° C. for 4 hours. Recovery: Aqueous 50 percent sodium hydroxide (246 parts) was added to the stirred mixture over a 2 hour period. An aqueous and organic layer resulted which were separated. The upper toluene layer was dried by azeotropic distillation. Analysis of this toluene layer revealed the presence of d-pseudoephedrine in 98.7 percent of theoretical yield, based on starting materials, and 1.3 percent of unreacted l-ephedrine. This toluene solution was cooled to approximately −5° C. which caused the d-pseudoephedrine to precipitate. The d-pseudoephedrine was collected by filtration, dried under vacuum and analyzed. The dried product represented a 91 percent overall yield of d-pseudoephedrine and had an analysis of 99+ percent purity.

EXPERIMENT 2

This reaction was carried out in essentially the same manner except that the acylating reagent used in Step I was propionic anhydride instead of acetic anhydride. Here, the reaction was conducted by blending l-ephedrine (41 parts) with propionic anhydride (75 parts) and 300 parts of toluene. The resulting toluene solution was heated at 110°–115° C. for 12 hours. Then, anhydrous HCl (9.3 parts) were added and the mixture heated for an additional hour at 90° C. Aqueous HCl (131.5 parts water and 18.5 parts HCl) was added and the reaction mixture heated for 4 hours at 85°–90° C. Finally, aqueous 50 percent sodium hydroxide (200 parts) was added, the organic and aqueous phases separated, the organic toluene layer dried by azeotropic distillation and analyzed. The toluene layer contained 98.5 percent of d-pseudoephedrine and 1.5 percent of unreacted l-ephedrine. The toluene solution was cooled to 0° C. and 37 parts (92 percent of theory) of d-pseudoephedrine recovered as a crystalline solid.

EXPERIMENT 3

In this experiment 2,2-dimethylpropionic anhydride was used as the acylating reagent in Step I. The reaction was otherwise conducted in a manner analogous to Experiment 2. The final toluene solution contained 98.4 percent of the d-pseudoephedrine and 1.6 percent of unreacted l-ephedrine. Upon cooling, 18.1 parts (87 percent of theory) of d-pseudoephedrine was recovered as a crystalline solid.

EXPERIMENT 4

In this experiment benzoic anhydride was used as the acylating reagent under conditions analogous to Experiment 2. In this experiment, however, the reaction of the oxazolinium salt with aqueous HCl (Step III) was run for 16 hours at 85°–90° C. The workup was the same and the toluene layer contained approximately 97.2 percent d-pseudoephedrine and 2.8 percent unreacted l-ephedrine. Upon cooling, the recovered yield of d-pseudoephedrine was approximately 84 percent.

EXPERIMENT 5

Under similar conditions, ethyl acetate was used as the acylating reagent. The final toluene solution contained 72 percent of theory of d-pseudoephedrine and 28 percent of unreacted l-ephedrine.

EXPERIMENT 6

Under similar conditions, formic acid was used as the acylating reagent and the conversion of l-ephedrine to d-pseudoephedrine was approximately 62 percent.

EXPERIMENT 7

Under similar conditions, benzoic acid was used as the acylating reagent and the conversion to d-pseudoephedrine was approximately 40 percent.

EXPERIMENT 8

Essentially identical results to Experiment 1 were obtained when concentrated sulfuric acid was used in place of anhydrous HCl in Step II of the reaction. All other conditions were essentially the same as in Experiment 1.

EXPERIMENT 9

Likewise, essentially identical results to Experiment 1 were obtained using trifluoroacetic acid in place of anhydrous HCl in Step II of the process.

EXPERIMENT 10 l-Ephedrine diacetate was prepared by reacting l-ephedrine with acetic anhydride in benzene solution. This benzene solution was dried by passing it through a column of "K-type" DOWEX® ion-exchange resin. Anhydrous HCl (0.07 mol) was added as a gas to an aliquot of the predried l-ephedrine diacetate solution (0.05 mole of l-ephedrine and 80 ml of benzene) and the solution heated at 50° C. for 0.5 hours. During this time an oil precipitated. Benzene and other volatiles were removed from the reaction mixture under vacuum leaving a heavy viscous oil as the residue. This oil was soluble in water and acetone at room temperature and contained 2,3-dimethyloxazolinium chloride as the predominant ingredient.

The above oxazolinium chloride (as the oil) was dissolved in approximately 50 ml of water and 70 percent perchloric acid added. A crystalline solid immediately precipitated which was quickly filtered and dried at 60° C. under reduced pressure. This solid product was 2,4-dimethyloxazolinium perchlorate. The product structure was confirmed by nuclear magnetic resonance and infrared spectroscopy and by elemental analysis. This oxazolinium perchlorate hydrolyzed on treatment with water over a period of 2 to 3 hours giving a product whose nuclear magnetic resonance spectrum was consistent with the following structure:

$$\begin{array}{c} \overset{\oplus}{N}H_2CH_3 \quad ClO_4^{\ominus} \\ | \\ C_6H_5CH-CH-CH_3 \\ | \\ O-C-CH_3 \\ \| \\ O \end{array}$$

Both oxazolinium salts described above reacted with aqueous HCl to give d-pseudoephedrine hydrochloride.

Other oxazolinium salts can be similarly prepared and used in the preparation of threo isomers of the 1-aryl-1-hydroxy-2-methylaminopropanes.

We claim:

1. The threo isomer of an oxazolinium salt corresponding to the formula in which R is a methyl or ethyl group, Ar is a phenyl or inertly-substituted phenyl wherein the inert substituent is selected from 1 to 4 carbon alkyl, methoxy and chloro group and $A^{\ominus}$ is an inert neutralizing anion of a strong inorganic protic acid.

2. The oxazolinium salt defined by claim 1 wherein R is methyl, Ar is phenyl, and $A^{\ominus}$ is $Cl^{\ominus}$, $ClO_4^{\ominus}$ or $HSO_4^{\ominus}$.

3. The oxazolinium salt defined by claim 2 wherein $A^{\ominus}$ is $Cl^{\ominus}$.

4. A process for preparing a threo compound defined by claim 1 comprising the step of reacting by contacting an O,N-diacylated product of an erythro isomer of a 1-aryl-1-hydroxy-2-methylaminopropane with an anhydrous or substantially anhydrous strong inorganic protic acid wherein the diacyl groups are those from the acylating reagent group of ketene, acetic acid, propionic acid, butenoic acid, octanoic acid; acetyl chloride, propanoyl chloride, benzoyl chloride; acetic anhydride, propionic anhydride, benzoic anhydride, phthalic anhydride; and the methyl or ethyl ester of one of acetic acid, propionic acid, butyric acid and hexanoic acid.

5. The process defined by claim 4 wherein said process is conducted in the presence of an inert reaction solvent or diluent.

6. The process defined by claim 5 wherein said reaction solvent or diluent is toluene.

7. The process defined by claim 4 wherein the O,N-diacylated product is the O,N-diacetyl product.

* * * * *